US011416811B2

(12) United States Patent
Bradley et al.

(10) Patent No.: US 11,416,811 B2
(45) Date of Patent: Aug. 16, 2022

(54) SYSTEM AND APPARATUS FOR VIRTUAL REALITY SMART INVENTORY MANAGEMENT

(71) Applicant: Data Vault Holdings, Inc., New York, NY (US)

(72) Inventors: Nathaniel T. Bradley, Tucson, AZ (US); Joseph McGovern, Seaford, NY (US)

(73) Assignee: Data Vault Holdings, Inc., New York, NY (US)

( * ) Notice: Subject to any disclaimer, the term of this patent is extended or adjusted under 35 U.S.C. 154(b) by 493 days.

(21) Appl. No.: 15/799,691

(22) Filed: Oct. 31, 2017

(65) Prior Publication Data

US 2018/0121869 A1     May 3, 2018

Related U.S. Application Data

(60) Provisional application No. 62/415,379, filed on Oct. 31, 2016.

(51) Int. Cl.
*G06Q 10/08*     (2012.01)
*G06Q 50/22*     (2018.01)
*G06T 11/60*     (2006.01)

(52) U.S. Cl.
CPC .......... *G06Q 10/087* (2013.01); *G06Q 50/22* (2013.01); *G06T 11/60* (2013.01)

(58) Field of Classification Search
CPC combination set(s) only.
See application file for complete search history.

(56) References Cited

U.S. PATENT DOCUMENTS

| | | | |
|---|---|---|---|
| 7,685,023 B1 * | 3/2010 | Abraham et al. | |
| 7,962,956 B1 * | 6/2011 | Liao et al. | |
| 8,311,906 B1 * | 11/2012 | Campbell et al. | |
| 10,163,071 B1 * | 12/2018 | Quan et al. | |
| 2001/0051905 A1 * | 12/2001 | Lucas | |
| 2003/0216969 A1 * | 11/2003 | Bauer | |
| 2005/0289020 A1 * | 12/2005 | Bruns et al. | |
| 2010/0138037 A1 * | 6/2010 | Adelberg et al. | |
| 2010/0161345 A1 * | 6/2010 | Cain et al. | |
| 2013/0231775 A1 * | 9/2013 | Jeffries et al. | |
| 2014/0156470 A1 * | 6/2014 | Raman | |
| 2014/0304123 A1 * | 10/2014 | Schwartz | |
| 2015/0046363 A1 * | 2/2015 | McNamara et al. | |
| 2016/0078264 A1 * | 3/2016 | Armstrong et al. | |
| 2016/0364681 A1 * | 12/2016 | Andrus | |
| 2017/0213186 A1 * | 7/2017 | Grifoni | |
| 2018/0053141 A1 * | 2/2018 | Shydo, Jr. | |
| 2019/0244164 A1 * | 8/2019 | Emert et al. | |

* cited by examiner

*Primary Examiner* — Michael Tomaszewski
*Assistant Examiner* — William T. Monticello
(74) *Attorney, Agent, or Firm* — Goodhue, Coleman & Owens, P.C.

(57) ABSTRACT

A system, method, and apparatus for logistics management. Inventory is received for storage at a physical storage location. The inventory is associated with an identifier. The inventory is stored in a location. The inventory is associated with the location. A system is updated with the inventory information including at least the identifier and the location for subsequent utilization. A virtual reality environment is shown to a number of users mirroring the physical storage location and movements of the inventory within the physical storage location.

20 Claims, 4 Drawing Sheets

FIG. 1

SYSTEM AND APPARATUS FOR VIRTUAL REALITY SMART INVENTORY MANAGEMENT

PRIORITY STATEMENT

This application claims priority to U.S. Provisional Patent Application 62/415,379, filed on Oct. 31, 2016, and entitled System and Apparatus for Virtual Reality Smart Inventory Management, hereby incorporated by reference in its entirety.

BACKGROUND

I. Field of the Disclosure

The illustrative embodiments relate to logistics tracking. More specifically, but not exclusively, the illustrative embodiments relate to a system, method, and apparatus for performing logistics management of inventory.

II. Description of the Art

The need for logistical information has increased exponentially in recent years. This is in part based on the mobility of individuals, families, companies, and organizations. In addition, developing technologies have made it so that users expect more data, information, and control particularly for their associated businesses, services, and organizations.

SUMMARY OF THE DISCLOSURE

One exemplary embodiment provides a system, method, and apparatus for logistics management. Inventory is received for storage at a physical storage location. The inventory is associated with an identifier. The inventory is stored in a location. The inventory is associated with the location. A system is updated with the inventory information including at least the identifier and the location for subsequent utilization. In another embodiment, the system may include a processor for executing a set of instruction and a memory for storing the set of instructions. The set of instructions may be executed by the processor to implement the method described above.

In another embodiment, a virtual reality environment is shown to a number of users mirroring the physical storage location and movements of the inventory within the physical storage location.

BRIEF DESCRIPTION OF THE DRAWINGS

Illustrated embodiments of the present invention are described in detail below with reference to the attached drawing figures, which are incorporated by reference herein, and where.

DETAILED DESCRIPTION OF THE DISCLOSURE

Figure 1:
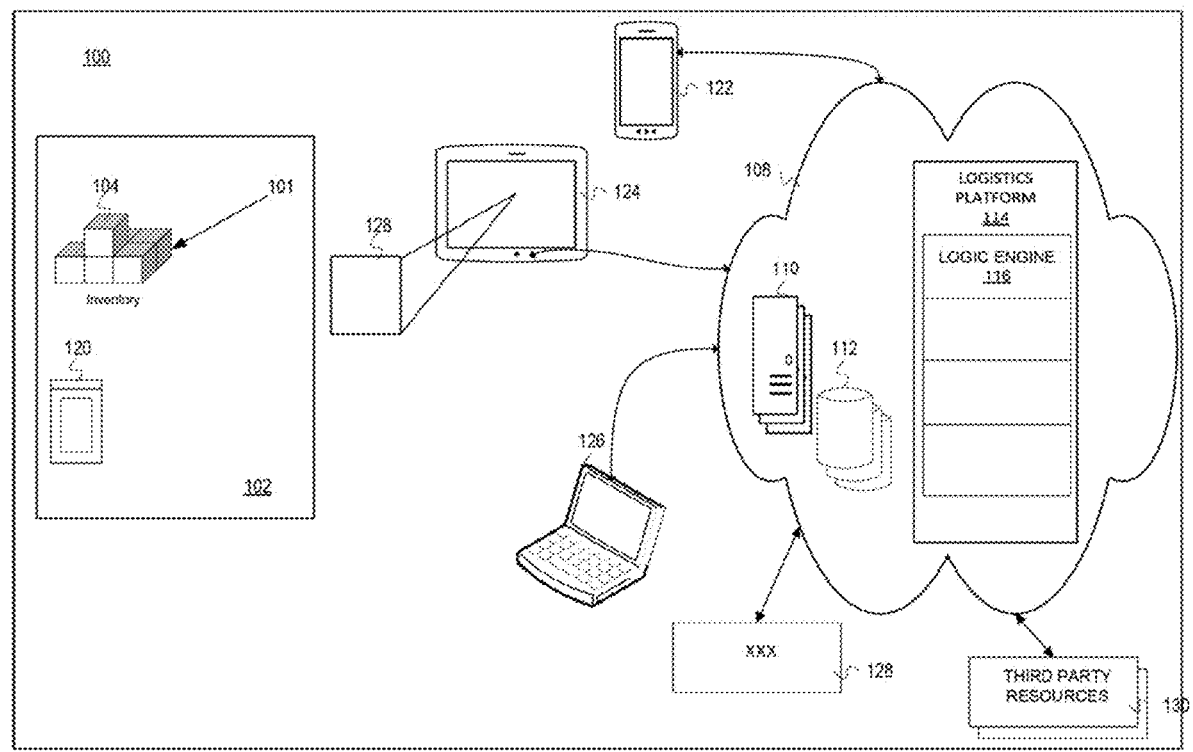
FIG. 1 is a pictorial representation of a system for managing inventory at a physical storage location in accordance with an illustrative embodiment.

The illustrative embodiments provide a system, method, and apparatus for logistics tracking. In one embodiment, the system may detect, decode, and retransmit product information and an inventory data topology. The inventory and logistics tracking embodiments herein described may be placed at the entrance as and exits of real-world retail, service, storage, or other product or inventory based environments. For example, the environments may represent an enclosure, compound, yard, building, or other physical storage location.

In one embodiment, the term physical storage location, area, or enclosure includes, but is not limited to, inventory storage warehouses, retail and merchant storage locations, inventory storage rooms, storage closets, inventory closets, cabinets, storage compartments, multi-shelled storage units, multi-product storage environments, multipurpose shelves, shelf free storage spaces for storing open or boxed inventory, storage carts, ambulatory cards, portable cabinets, multifaceted storage compartments, multi-drawer compartments, enclosed drawer compartments, containers, open air yards, residences, businesses (e.g., retailers, hospitals, distribution centers, etc.), or other locations or environments that store variety of products, inventory, or equipment. The term inventory as used herein may refer to products, merchandise, equipment, items, components, or any other physical component, device, or unit.

In one embodiment, two or more inventory and logistics tracking systems or apparatus may be used at a physical location with one or more entry points. The apparatus may be installed in any suitable position of an entry point and provisions for the storage tracking, logistics, and secure distribution of inventory.

In one embodiment, the system is placed at a physical location, such as an entry/exit point. The system may be positioned on an inner or an outer portion of the entry or access point to the physical storage location. In another embodiment, the system may include a network of devices or apparatus capable of a variety of reporting, tracking, and management activities that may be placed in any number of locations of the physical storage location. For example, the embodiments may be utilized for large-scale tracking of inventory in multi-level storage spaces and large warehouse environments.

The inventory in a physical storage location may be registered, assigned, associated, and recognized. For example, the inventory may be associated with a particular location, time, movement speed, movement direction, process, or so forth. In one embodiment, the illustrative embodiments may be performed by a software platform that is integrated with, connected to, or installed within a system as described herein.

The system may recognize and associates product data with product environment data through any single or combined identifier (e.g., barcode, serial number, product data, product environment identifier data, QR code, etc.). The data from the system including inventory data, product data, and location data, may be utilized to create a virtual representation of inventory at the physical storage location. Thus, tracking and management of inventory may be performed in real-time.

FIG. 1 is a pictorial representation of a system 100 for managing inventory at a physical storage location 102 in accordance with an illustrative embodiment. In one embodiment, the system 100 may be installed at a location 101 of the physical storage location 102 for storing inventory 104. The physical storage location 102 may include any number of rooms, compartments, closets, drawers, separators, dividers, or separate facilities. The system 100 may include any number of devices, components, sub-systems, and so forth. In one embodiment, the system 100 any number of apparatus, such as apparatus 120.

The system 100 may be installed at the physical storage location 102 to track and control the inventory 104 on-site or remotely through a direct or indirect (e.g., one or more local area networks, secured networks, Wi-Fi networks, cellular networks, etc.) physical or wireless connections. In one embodiment, the system 100 may communicate through a network 108. The network 108 may represent one or more mobile or wireless networks. The network 108 may also represent a centralized computer network. The communications performed through the network 108 are secure. Any number of encoding, encapsulation, packetization, or other techniques may be utilized. The system 100 and the associated network 108 may include any number of servers 110 may be integrated with or in communication with the network 108. The servers 110 may utilize databases 112 to store applicable information and generate models, simulations, and environments associated with the physical storage location 102 and the associated inventory 104.

In one embodiment, the servers 110 may implement the processes performed by the system 100. The servers 110 may execute a logistics platform 114. The logistics platform 114 may include a logic engine 116 and any number of modules for tracking requests, orders, movements, stocking requests, authorization information, and so forth. Any number of electronic devices 122, 124, 126 may be utilized. In one embodiment, the electronic devices 122, 124, 126 may execute software, programs, or application 128 to implement commands and view information and data applicable to the system 100. In one embodiment, the application 128 may be utilized to display a virtual environment for managing the system 100 and the inventory 104. Although not shown, any number of augmented reality, virtual reality, gaming, or other systems may be utilized in conjunction with the system 100 to manage, display, or view applicable information and data.

As shown, the apparatus 120 is installed at the location 101 of the physical storage location 102. In one embodiment, the apparatus 120 may represent a node of the system 100. Any number of additional apparatus/nodes may be utilized based on the size, complexity, entries/exits, and logistical information sought by the system 100. The apparatus content may be utilized to provide a link and information associating specific locations, inventory data, and virtual and real-world maps, logistics, simulations, and data.

The apparatus 120 recognizes each item of inventory 104 and associates the product to an environment, date/time, action being performed on the item of inventory 104, and other information utilizing the identifier. In one embodiment, the apparatus 120 may include any number of cameras, scanners, microphones, scales, or so forth for identifying the unique identifier utilized for the inventory 104.

The identifier may represent a UPC, Point of sale identifier, barcode, QR code, radio frequency identification tag (RFID), tag systems, custom codes, video or image recognition, weight, P-chip, or other known product or inventory tracking identifiers, chips, transceivers, active/passive components, and so forth. In one embodiment, the apparatus 120 may include any number of camera/optical systems (e.g., X-rays, infrared, visible light, etc.), microphones, scales, or so forth for determining the size, shape, sound, weight, and so forth of the inventory 104. For example, the apparatus 120 may be a scanner including a processor, memory, and scanning components.

In one embodiment, the system 100 may associate the inventory 104 with the location 101 utilizing a planogram. A planogram is a direct representation of a physical environment, such as the physical storage location 102. The planogram may include the layout, structure, and configuration of the inventory 104 including specifics, such as the exact orientation, placement (e.g., x, y, z, orientation) of the inventory 104 in the physical storage location 102.

The planogram for the location 101 may exist or may be initially created to cover the entire inventory 104 of products contained in the physical storage location 102. The planogram may also be created via a picture, visual image, rendering, drawing, model, augmented reality visualization, or other information about the inventory 104 in the physical storage location 102. The planogram may be modified with a new planogram identifier for each new unique item or product that is introduced into the inventory 104. In one embodiment, the system 100 or the apparatus 120 may be automatically provisioned utilizing the items in the inventory 104.

The system 100 may create additional unique identifiers from inventory control forms or product numbers for the inventory 104. The numbers may come from forms, reports, templates, files or documents, such as reorder forms. The files documents may be modified with unique identifiers utilized and combined as needed as a substitute for a planogram in environments with less stringent product organization requirements or where a limited variety of products are tracked.

In other embodiments, additional unique identifiers may be created across each product including the item, brand, model, and product set and may include a physical and/or virtual tag associating the specific item of the inventory 104 with the unique identifier, mark, physical attribute, weight, position, storage/shipping instructions, signal broadcast, or so forth.

Each data item associated with the inventory 104 may be assigned a unique identifier and multiple data points that may be included within transmission data and may be utilized in combination with a product identifier.

In one embodiment, the system 100 may utilize any number of sensors. The type and configuration of sensors as well as code or data points may be determined by the user of the systems based on user/system preferences, inventory size, method, brand, costs, and reusability. The data captured by the system 100 may not require tags, identifiers, or sensors. For example, the inventory 104 may be tracked via a number of data and image capture tools. The system 100 may utilize any number of light sensors, optical sensors, barcode sensors, RFID, GPS, electromagnetic frequency, motion detectors, light sensing sources, telemetry, beacons, tones, P-chips or other inventory tracking devices and mechanisms that may register the inventory 104 quantities for inventory control, logistics, and reorder tracking.

The inventory 104 may also include visual data points. The visual data points may be displayed as graphics on the item of the inventory 104 or on the associated packaging materials and may be readily modified based on specific needs or requirements. The data points utilized for the inventory 104 may also come from secondary sensor beacons that may be placed before, during, or after manufacturing, shipping, distribution, or sales.

The system 100 may create a virtual representation of the physical storage location 102 and the associated inventory 104. In one embodiment, the apparatus may register all data points of information and inventory 104 associated with the physical storage location 102 associated the inventory 104 with the unique identifiers.

In one embodiment, a distinct locator for each piece of inventory 104 from a product set of identical products, locator beacons for the same product set, or UPC code may be associated and distinguished from one another through the unique location and product identifier in combination with a varied range of modulations or frequency rate variances within the locator beacons frequency ranges. Data for the same product set or identifier in the same location may be associated and distinguished from one another through user based modifications in the planograms layout or inventory identifiers.

The physical storage location 102 and unique identifier data may be virtually tracked from the location 101 each time the inventory 104 passes by or is opened proximate the apparatus 120. Any number of queries, searches, or processing requests may be performed utilizing the servers 110 or the databases 112 regardless of whether the user physically or remotely interfaces with the system 100.

Invocation or activation of the system 100 may be implemented automatically or in response to a user request. In one embodiment, the system 100 automatically performs logistics and inventory actions based on actions of the users, robotics, machines, or other equipment or devices within the physical storage location 101 with respect to the inventory 104. Logistics requests may be received at any time by the system 100. In one embodiment, upon receiving a request for an item of the inventory 104, the item may be removed from the location 101. The apparatus 120 may detect the change in location or transfer request and associated the updated information with the item. For example, the unique identifier may specify the movement, employee/manager authorizing or performing an associated activity, and the activity performed.

The data from the item of inventory 104 may be amended and tracked through the network 108. An updated visual representation of the item of inventory 104 may also be updated based on movements, transfers, exits, relocation, storage, damage, usage, or other specified activity or action within the physical storage location 101.

The illustrative embodiments contemplate invocation of the systems and methods herein described without an item of inventory 104 being removed. For example, a spot check, audit, or stocking process may be utilized to ensure that inventory levels and locations are appropriate.

Items of inventory 104 that are moved, used, removed, or damaged are tracked with the data and information being uploaded, stored, and amended utilizing the servers 110 and the databases 112. In one embodiment, items of inventory 104 that are removed from the location 101 trigger an alert for a reorder or status check. As a result, the items of inventory 104 may be restocked daily or as needed by product vendors, bulk suppliers, manufacturers, internal processes, or so forth. The system 100 may be utilized to ensure that daily product sales and usage of the inventory 104 are tracked to maintain adequate or determined levels of inventory 104.

Logistics based instructions may be created from any local or remotely located device (e.g., computer, smart phone, tablet, dedicated device, etc.). The instructions may be received at the apparatus 120, servers 110, or other central processing systems that may be part of the system 100. In one embodiment, the servers 110 may represent a cloud system that provides a virtual representation of the inventory 104 as well as logistical instructions associated with the items of inventory 104.

The logistical requests processed by the system 100 may initiate a network based inventory check of all physical storage locations 101 associated with the system 100 (any number of locations may be associated with the system 100). The inventory check matches the request items of inventory 104 with their associated location, processing instructions, and other relevant information utilizing the identifier. A logistical order related to an item of inventory is confirmed with initiates the creation of the related real world logistical instructions correspond to the items of inventory 104. Through instructions within a virtual reality environment provided through the servers 110 of the system 100, changes may be made that result in the processing of virtual inventory. The virtual management of the inventory 104 and associated changes are linked with and utilized to perform location and processing of the actual inventory 104 of the physical storage location 102. The logistical instruction allows for real world items of inventory 104 to be made physically moveable from one location 101 to any additional connected physical environments (not shown). The apparatus 120 may perform tracking of movements (e.g., moved for processing, restocked, shipped from the physical storage location 102, etc.) and inventor 104 management. The instructions may also be tied to a planogram or additional instructions as to where the item of inventory 104 is current located, how it is to be handled/processed, and where the item of inventory 104 will be relocated or used.

The system 100 recognizes logistics requests, indicates the location of the inventory 104, processes logistics instructions, and manages the retrieval process from end-to-end. Once all logistical steps in the process are completed the changes are mirrored between the locations (e.g., physical environment of the location 102) and the virtual reality environments. In one embodiment, changes to the virtual environment are utilized to mirror in real-time the changes to the physical environment for fast-paced and dynamic physical storage locations 102.

In one embodiment, the system 100 may be utilized for patient based inventory logistics. Each request may be sent through remotely or locally utilized devices to locate a specific item of the inventory 104 at the location 101. As noted, the logistics request may relate to a piece of durable medical equipment (DME), medical product, medicines, or an item of medical inventory. The request may require a verification of a doctor (e.g., prescription, authorized, order, etc.) to confirm the request before any processing is implemented. The apparatus 120 as well as other components of the system 100 may track and verify applicable information about the patient and item in real-time to ensure authorized and appropriate usage (e.g., patient data, insurance, medical necessity, prescriptions, doctors' orders, etc.). Once the system 100 verifies the location 101 of the item of inventory 104 from the original request, the location 101 of the item of inventory 104 is identified utilizing the virtual location associated with the physical storage location 102.

The system 100 may take an inventory tally and determined the nearest location with the item of inventory 104 requested to most efficiently process the request. The response of available items of inventory 104 suitable for the patient may include duplicate items availability in the event of a delay or further issue. The apparatus 130 may anticipate the removal of an item of inventory 104 through tracking and verification. For example, any number of rooms, locks, entry points, scanners, guards, or other systems may be utilized as secondary security measures to prevent unauthorized removal of inventory 104 from the physical storage location 102. The apparatus 120 verifies the movement and implemented actions within the physical storage location 102. In addition, the databases 112, planograms, virtual environments, and other data and information communicated to several users utilizing the system 100 may be updated in real-time or near real-time.

Within the medical field products are sometimes billed incrementally over product usage periods. For every billing period, multiple payer scenarios exist. The illustrative embodiments contemplate the sharing of costs between several insurers, patients, or groups. In one embodiment, pairing of product inventory 104, patient data, authorized orders, doctor prescriptions, and hospital information (e.g., physical storage location 102) along with primary and secondary care payer insurance may be combined to create an incrementally tiered payment structure for multi-payer or multi-insurer scenarios. Utilization is tracked to allocate cost utilizing the identifiers associated with the inventory 104 and the databases 112. Cost may be associated based on one or more of time-in-use, times used, an hourly-rate for a device and/or medical professionals, fixed fees, or so forth.

In one embodiment of a tiered payer scenario, patient data may be individually and uniquely associated with each patient's insurance provider through their patient and insurer data. This data may be included in the patient's hospital bracelet, QR code, or other data or code. The associated data and logistics information requests may be included in prescriptions, doctors' orders, treatment plans, and may automatically be extracted or entered/requested manually by a party associated with the patient. This information may also be added, updated, and managed through the databases 112.

In a multiple insurer scenario, a rate card formula may be contemplated that is calculated based on the time the apparatus 120 associates and connects the patient and insurer data as well as confirmation of the prescription, order, or treatment plan of a medical professional. The system 100 may also calculate and assign tiered payments or other payment structures or plans based on the applicable insurance information. In scenarios where products are billed incrementally over product usage periods a similar rate card formula may be calculated.

In one embodiment, the physical storage location 102 may represent a secured environment, such as a retail location, secured room, storage locker, cabinet, storage compartments, closet or other types of physical locations or enclosures. Entry to the secured location may be dependent on a key, keycard, ID card, RFID tag, FOB, password, voice recognition, finger print, retinal scan, or other biometric or user specific indicators. As a result, inventory 104 as well as users entering and leaving the physical storage location 102 may be tracked in detail (e.g., time of entry, time of departure, time at the physical storage location 102, etc.).

In one embodiment, an applicable room is equipped with the apparatus 120 that may recognize the specific data and information associated with the inventor 104, users, or so forth. Data may be individually associated with each specific item of inventory through a product specific identifier and may include a unique location identifier that ties a specific item of inventory 104 to the specific location 104.

In one embodiment, the apparatus 120 may detect when each item crosses the threshold of the secured location and is now linked with a removing person/device and potentially a new location. The sensor may detect the removal or logistics requests made on any piece of equipment or item of inventory equipped with product data. The removal by a person with a secured clearance may act as a check-out, purchase, or usage validation. Where there is no authorization for the item of inventory 104 to be removed, an alarm may sound. In other embodiments, secure communication alerts, messages, or indicators may also be sent through text, email, phone call, in-app message, or so forth. The illustrative embodiments may be applicable to retail operations, hospitals, nursing homes, durable medical equipment consignment operations, airlines, prisons, athletic equipment tracking, band equipment tracking, technology data centers, laboratory sample management, logistics and shipping port management, and maritime operations.

Figure 2:
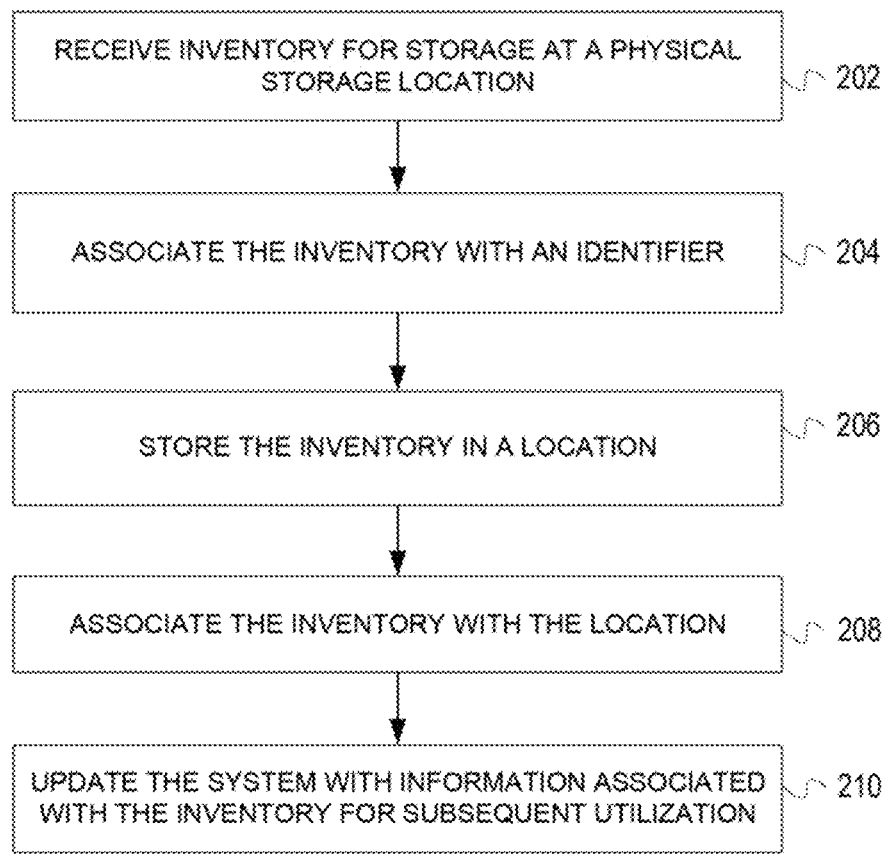
FIGS. 2-3 are flowcharts of a process for logistics management in accordance with an illustrative embodiment.

FIG. 2 is a flowchart of a process for logistics management in accordance with an illustrative embodiment. In one embodiment, the process of FIG. 2 may be implemented by a system or apparatus, such as those shown in FIG. 1. In one embodiment, the process may begin by receiving inventory for storage at a physical storage location (step 202). The inventory may be delivered automatically or utilizing any number of human interactions. For example, the deliveries may be performed by an automated system (e.g., conveyors, vacuum tubes, etc.), cart or drone. In another example, the deliveries of the inventory may be performed by an employee, contractor, or other responsible party assigned to service the physical storage location.

Next, the system associates the inventory with an identifier (step 204). In some embodiments, the identifier may be included as an integrated part of the inventory or an attached label. In other embodiments, the identifier may be assigned to the inventory. For example, even though the inventory may include a barcode, a location or use-based identifier may be additionally assigned to each piece of inventory. In some embodiments, the identifier may be assigned utilizing an RFID chip, label, sticker, or so forth. For example, a robotic assistant may automatically print and attach labels.

Next, the system stores the inventory in a location (step 206). The inventory may be stored in the facility utilizing any number of storage containers or techniques. In some embodiments, the inventory may represent high-value, flammable, addictive, or dangerous content that are secured using safes, containers, partitions, additional safety systems, or so forth. The location may include any number of security systems, measures, devices, monitors, and components.

Next, the system associates the inventory with the location (step 208). In one embodiment, the unique identifier associated with the inventory may also be associated with the location. For example, the inventory may be associated with the location utilizing one or more electronic communications through a signal, communication, or network. The association of the inventory with the identifier and the location (steps 204 and 206) may be stored in locally available devices or in devices that are remotely located (e.g., networked, cloud-based devices, etc.).

Next, the system updates the system with information associated with the inventory for subsequent utilization (step 210). In one embodiment, the system may utilize the applicable information to generate a virtual reality, augmented reality, or simulated environment showing all applicable inventory and the associated location of each piece of inventory. The system may make the inventory information utilizing one or more files, databases, programs, or other delivery systems. For example, the system may distribute inventory information to authorized users through a cloud-based system to ensure that applicable information regarding the utilization of the inventory (e.g., in-use, consumed, location, schedule, etc.) is updated in real-time or near real-time. In some embodiments, the system may update information and content based on the available of communications signals or networks.

Figure 3:
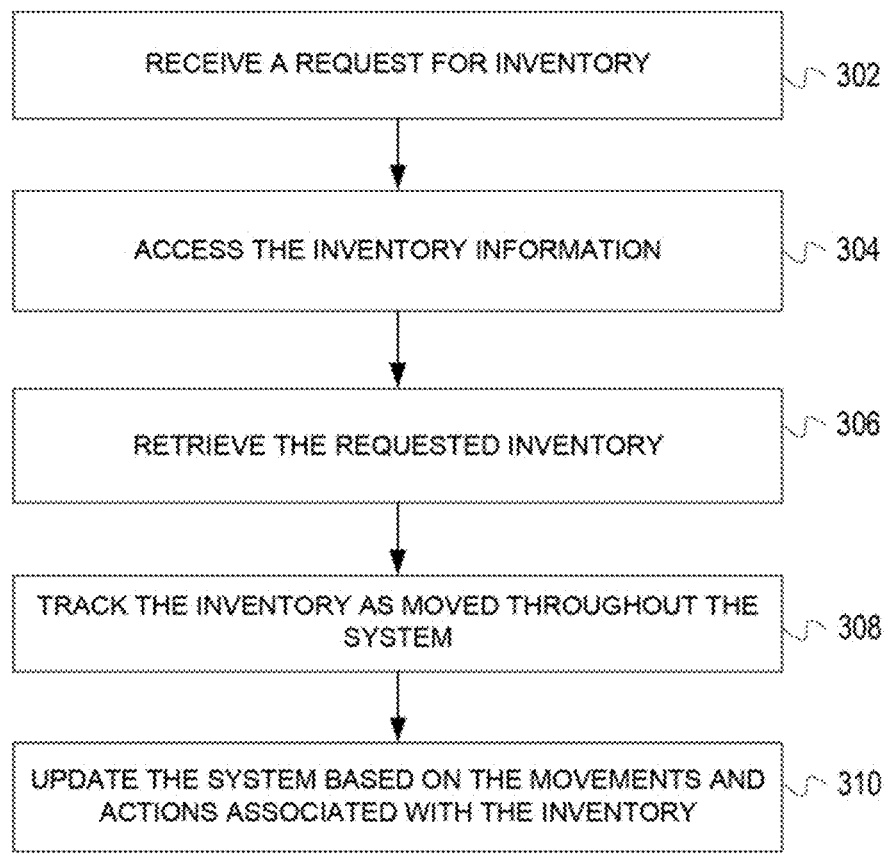

FIG. 3 is a flowchart of a process for further performing logistics management in accordance with an illustrative embodiment. The process may begin by receiving a request for inventory (step 302). The request may be received through one or more management platforms, systems, or software. For example, a request for a piece of equipment may be received through an inventory management portion of the system. The request may be performed based on feedback from a medical professional. In another embodiment, the request may be automatically generated in response to available information or details. For example, in response to an audio system monitoring the emergency room determining that an EKG may be required, an EKG cart may be allocated to the emergency room until retrieved by a medical professional.

Next, the system accesses the inventory information (step 304). The inventory information may include location, number of items, availability, personnel requirements, instructions-for-use, and so forth. The inventory information may include information regarding availability, utilization, delivery, safety procedures, applicable instructions, and so forth.

Next, the system retrieves the requested inventory (step 306). In one embodiment, one or more automated systems, such as robotic arms, robots, kiosks, drones, or so forth may be utilized. The system may also ensure retrieval of the inventory utilizing couriers, orderlies, nurses, doctors, caregivers, or other responsible parties.

Next, the system tracks the inventory as moved through the system (step 308). The system may include any number of locations including building, facilities, rooms, areas, spaces, or so forth. In some embodiments, the inventory may be moved multiple times based on a single request. The inventory may include durable medical equipment that is very expensive and has a long-life span. As a result, tracking the inventory to care for it may be very important.

Next, the system updates the system based on the movements and actions associated with the inventory (step 310). The system may release the inventory for movement, track the movement of the inventory, track utilization or consumption, and accept the inventory into one or more secondary locations or areas.

The processes illustrate various embodiments that may be implemented as described herein.

The illustrative embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computing system (or other electronic device(s)) to perform a process according to embodiments, whether presently described or not, since every conceivable variation is not enumerated herein. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or other communications medium.

Computer program code for carrying out operations of the embodiments may be written in any combination of one or more programming languages, including an object-oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (e.g., through the Internet using an Internet Service Provider).

Figure 4:
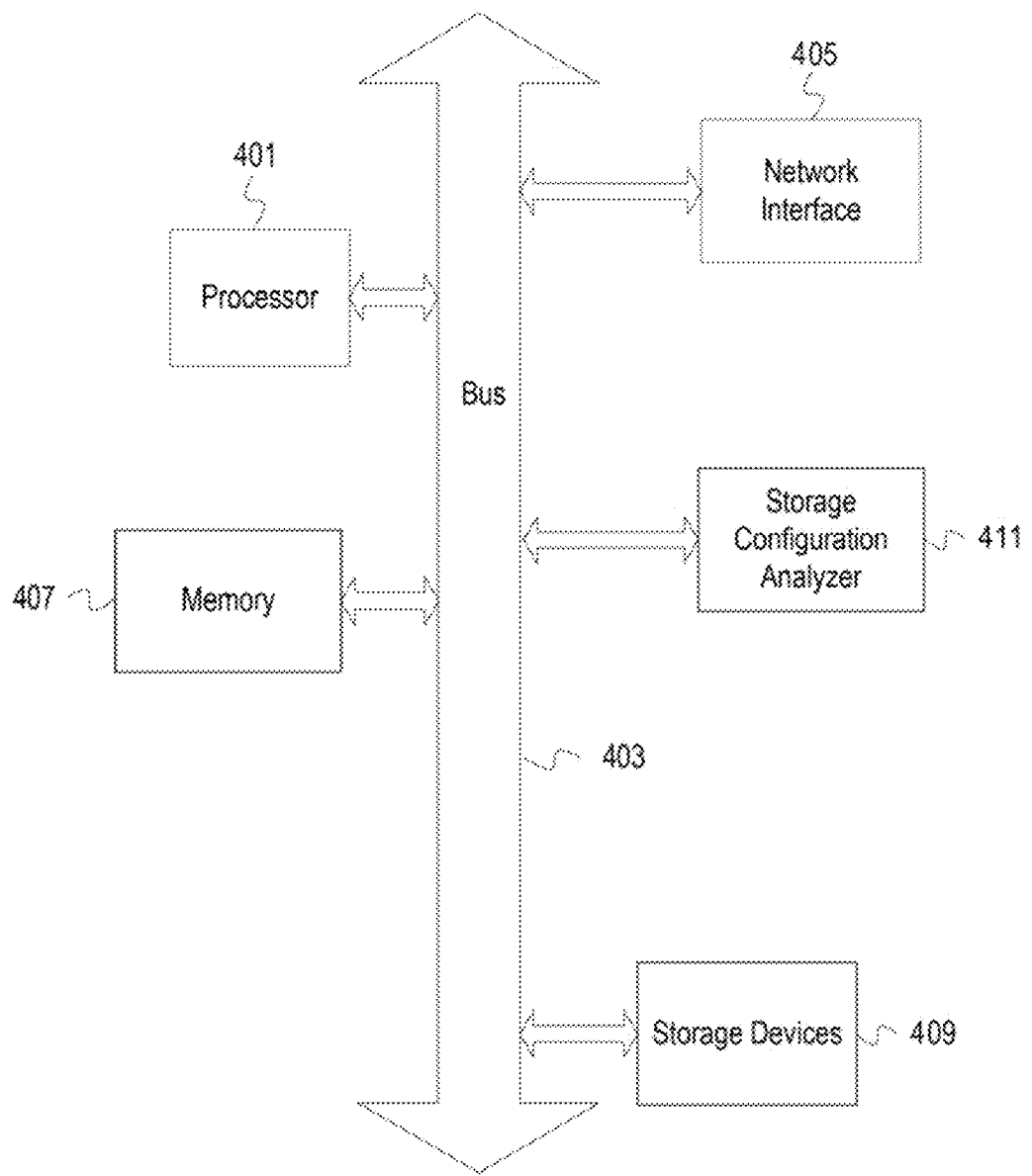
FIG. 4 is a pictorial representation of a computing device in accordance with an illustrative embodiment.

FIG. 4 depicts a computing system 400 in accordance with an illustrative embodiment. For example, the computing system 400 may represent all or portions of a device, such as the servers 100, apparatus 120, or electronic devices 122-126 of FIG. 1. The computing system 400 includes a processor unit 401 (possibly including multiple processors, multiple cores, multiple nodes, and/or implementing multi-threading, etc.). The computing system includes memory 407. The memory 407 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system also includes a bus 403 (e.g., PCI, ISA, PCI-Express, HyperTransport®, InfiniBand®, NuBus, etc.), a network interface 406 (e.g., an ATM interface, an Ethernet interface, a Frame Relay interface, SONET interface, wireless interface, etc.), and a storage device(s) 409 (e.g., optical storage, magnetic storage, etc.). The system memory 407 embodies functionality to implement all or portions of the embodiments described above. The system memory 807 may include one or more applications or sets of instructions for implementing a medical engine to communicate with one or more wireless earpieces. The medical engine may be stored in the system memory 407 and executed by the processor unit 402. As noted, the medical engine may be similar or distinct from a medical engine utilized by the wireless earpieces. Code may be implemented in any of the other devices of the computing system 400. Any one of these functionalities may be partially (or entirely) implemented in hardware and/or on the processing unit 401. For example, the functionality may be implemented with an application specific integrated circuit, in logic implemented in the processing unit 401, in a co-processor on a peripheral device or card, etc. Further, realizations may include fewer or additional components not illustrated in FIG. 4 (e.g., video cards, audio cards, additional network interfaces, peripheral devices, etc.). The processor unit 401, the storage device(s) 409, and the network interface 405 are coupled to the bus 803. Although illustrated as being coupled to the bus 403, the memory 407 may be coupled to the processor unit 401. The computing system 400 may further include any number of optical sensors, accelerometers, magnetometers, microphones, gyroscopes, temperature sensors, and so forth for verifying inventory and physical storage environmental conditions, such as motion, light, or other events that may be associated with the inventory or their environment.

The features, steps, and components of the illustrative embodiments may be combined in any number of ways and are not limited specifically to those described. In particular, the illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure.

The previous detailed description is of a small number of embodiments for implementing the invention and is not intended to be limiting in scope. The following claims set forth a number of the embodiments disclosed with greater particularity.

What is claimed is:

1. A method for logistics management, comprising:
    receiving inventory for storage at a physical storage location;
    automatically associating the inventory with an identifier in a system, utilizing one or more scanners physically integrated with the physical storage location, in response to movements of the inventory, wherein the one or more scanners communicate with the system through one or more networks;
    storing the inventory in a location of the physical storage location;
    automatically associating the inventory with the location in the system utilizing the one or more scanners proximate the location;
    automatically updating the system with 1) inventory information including at least the identifier and the location for subsequent utilization of the inventory, and 2) verification of the inventory information including at least whether the inventory is securely stored, in use at a secondary location, applicable damage, and usage level; and
    implementing a reorder for the inventory based on the inventory information.

2. The method of claim 1, further comprising:
    automatically updating the system with the location of the inventory in response to the inventory being moved within the physical storage location.

3. The method of claim 1, further comprising:
    removing the inventory from the system in response to the inventory being used up.

4. The method of claim 1, further comprising:
    receiving a request for the inventory;
    accessing the inventory information;
    retrieving the inventory utilizing the inventory information;
    automatically tracking the inventory utilizing the system as moved throughout the physical storage location; and
    updating the system based on movements, actions, and status associated with the inventory.

5. The method of claim 4, further comprising:
    verifying that a party associated with the request is authorized to request the inventory, wherein the retrieving is performed only if the party is verified.

6. The method of claim 5, wherein the inventory is medicine for a patient in a care facility.

7. The method of claim 5, wherein the inventory includes at least durable medical equipment and one-time use goods, and wherein the system includes at least servers and databases accessible through one or more networks.

8. The method of claim 4, wherein the one or more scanners are positioned at entry points for the physical storage location to track the inventory through the physical storage location.

9. The method of claim 1, further comprising:
    providing a virtual environment that mirrors the inventory in the physical storage location for managing the inventory.

10. A system for performing logistics management, comprising:
    one or more scanners for determining locations of inventory, the one or more scanners are physically integrated with the locations; and
    one or more servers in communication with the one or more scanners for associating unique identifiers and locations with the inventory, providing a virtual environment for managing the inventory, and reordering the inventory in response to information from the one or more scanners, wherein the one or more scanners 1) automatically track movements of the inventory through a physical storage location utilizing the unique identifiers and 2) utilization level of the inventory within the physical storage location based on information from the one or more scanners, wherein verification of the inventory is performed in response to the information from the one or more scanners.

11. The system of claim 10, wherein the inventory includes at least durable medical equipment and one-time use goods.

12. The system of claim 10, wherein the servers are accessible to a plurality of remote users utilizing a secure network for managing the inventory.

13. The system of claim 10, wherein the virtual environment is accessible through glasses, headsets, or electronic glass.

14. The system of claim 10, wherein the one or more scanners determine the location of the inventory within the physical storage location.

15. The system of claim 10, wherein the one or more servers determine whether a user or device is authorized to access the inventory, and wherein the one or more servers grant access for the user or device to move the inventory without setting off an alarm.

16. An apparatus for logistics management, comprising:
    a scanner for determining a location of inventory within a physical storage location and utilization of the inventory, wherein the scanner is physically integrated with the physical storage location;
    a memory for storing inventory information associated with the inventory; and
    a logic engine for managing the inventory information, wherein the logic engine associates an identifier and a location with each item of the inventory as part of the inventory information, wherein the logic engine stores the inventory information associated with movement and secure storage of the inventory within or outside the physical storage location, usage status, and applicable damage, and wherein the logic engine implements a reorder for the inventory based on the inventory information.

17. The apparatus of claim 16, wherein the logic engine generates a virtual environment modeling the inventory within the physical storage location.

18. The apparatus of claim 16, wherein the logic engine is a logistics platform executed to manage the inventory within the physical storage location.

19. The apparatus of claim 16, wherein the logic engine sets off an alarm in response to an unauthorized user or device accessing the inventory or movement outside the physical storage location.

20. The apparatus of claim 17, wherein the virtual environment is updated in real-time, and wherein the inventory includes at least durable medical equipment and one-time use goods.

\* \* \* \* \*